United States Patent [19]

Matsuura et al.

[11] Patent Number: 4,909,066
[45] Date of Patent: Mar. 20, 1990

[54] THICK-FILM GAS SENSOR OF A LAMINAR STRUCTURE AND A METHOD OF PRODUCING THE SAME

[75] Inventors: Toshitaka Matsuura; Keizo Furusaki; Akio Takami, all of Nagoya, Japan

[73] Assignee: NGK Spark Plug Co., Ltd., Nagoya, Japan

[21] Appl. No.: 281,881

[22] Filed: Dec. 8, 1988

Related U.S. Application Data

[63] Continuation of Ser. No. 876,002, Jun. 19, 1986, abandoned.

[30] Foreign Application Priority Data

Jul. 2, 1985 [JP] Japan ................... 60-143847

[51] Int. Cl.$^4$ ........................................... G01N 27/12
[52] U.S. Cl. ..................................... 73/27 R; 73/23
[58] Field of Search .................... 73/23, 27; 340/632, 340/634; 338/34; 427/125; 422/98; 204/421, 426

[56] References Cited

U.S. PATENT DOCUMENTS

| 4,221,827 | 9/1980 | Parry et al. | 427/12.5 |
| 4,225,634 | 9/1980 | Takaka et al. | 427/125 |
| 4,354,912 | 10/1982 | Friese | 204/426 |
| 4,413,502 | 11/1983 | Otha et al. | 338/34 |

FOREIGN PATENT DOCUMENTS

| 115837 | 6/1985 | Japan | 73/23 |
| 117140 | 6/1985 | Japan | 73/23 |

Primary Examiner—Hezron E. Williams
Attorney, Agent, or Firm—Fleit, Jacobson, Cohn, Price, Holman & Stern

[57] ABSTRACT

A gas sensor has a ceramic substrate carrying a pair of electrodes embedded therein, which substrate has an opening bored at a surface portion thereof so as to expose tip portions of the electrodes. A thick gas-sensitive film is provided at the opening in such a manner that a gap between the electrode tip portions is filled by the gas-sensitive film while the metallic material of the electrodes is caused to precipitate on the boundary between the electrodes and the gas-sensitive film, so that the performance characteristics of the sensor is stabilized and its durability is improved.

7 Claims, 4 Drawing Sheets

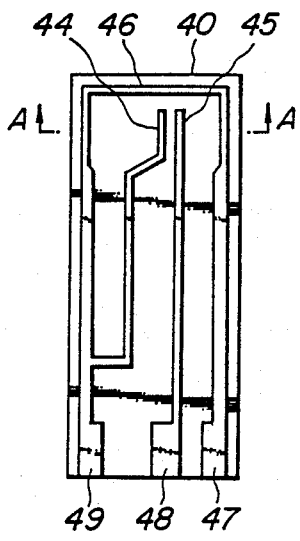
FIG_2
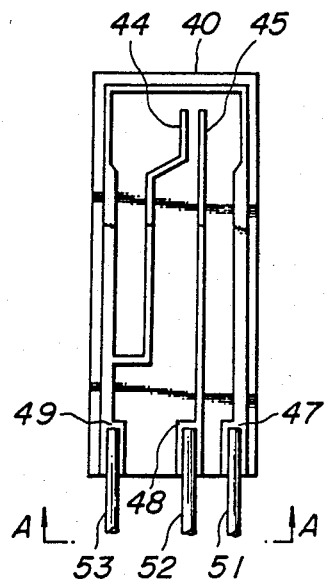
FIG_3
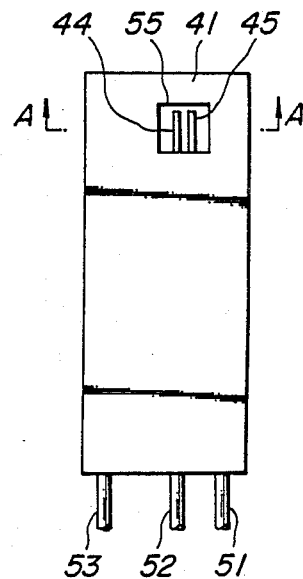
FIG_4
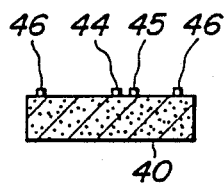
FIG_2A
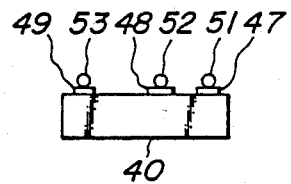
FIG_3A
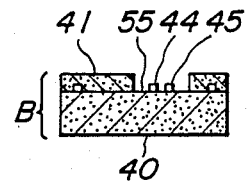
FIG_4A FIG._5 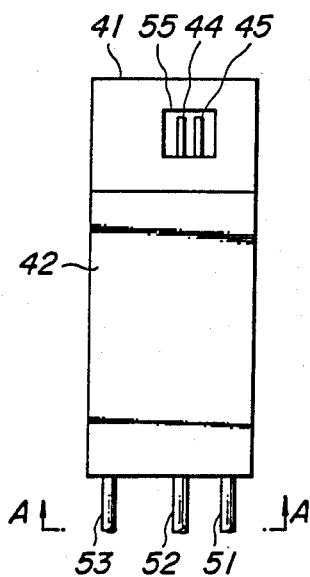
FIG._6 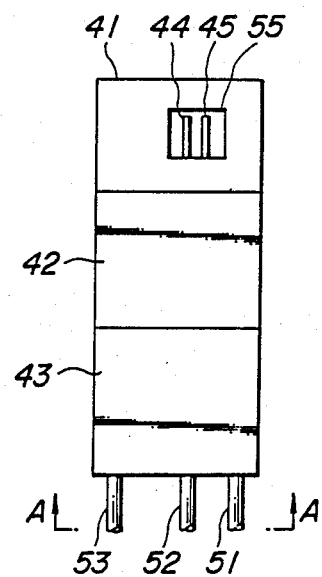
FIG._7 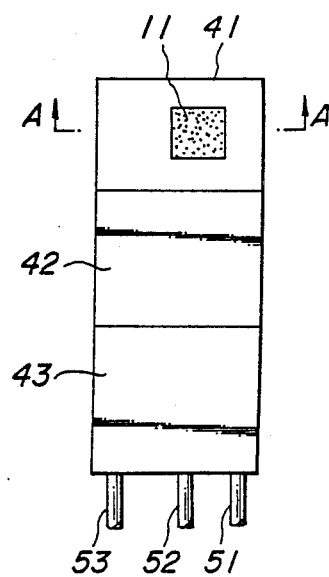
FIG._5A 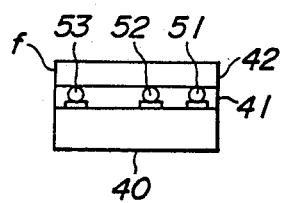
FIG._6A 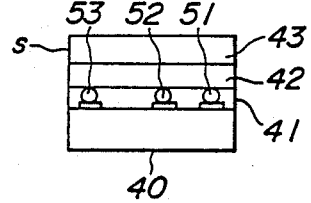
FIG._7A 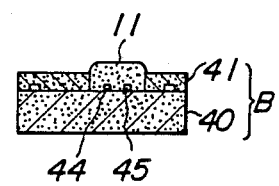

THICK-FILM GAS SENSOR OF A LAMINAR STRUCTURE AND A METHOD OF PRODUCING THE SAME

This application is a continuation, of application Serial No. 876,002, filed June 19, 1986 now abd.

BACKGROUND OF THE INVENTION

1. Field of the Invention

This invention relates to a thick-film gas sensor of a laminar structure and a method of producing the same. More particularly, the invention relates to an improvement in reliability and durability of a thick-film gas sensor of a laminar structure by preventing deterioration of its performance. The sensor comprises a ceramic substrate, a pair of electrodes disposed on the ceramic substrate and a thick porous gas-sensitive film extending across the electrodes while covering the electrode surfaces.

2. Related Art Statement

A typical thick-film gas sensor of a laminar structure of the prior art has a thick gas-sensitive film disposed on a flat substrate, as described in laid-open Japanese Patent Application No. 115,837/85, for example. The gas-sensitive film tends to be peeled off easily due to difference in thermal expansion between the substrate and gas-sensitive film.

The inventors disclosed an improvement in the adhesion of the gas-sensitive film to the substrate in their Japanese Patent Application No. 203,222/83, which improvement was achieved by roughening the substrate surface or by providing artificial undulations on the substrate surface.

Further study by the inventors has revealed that, although the adhesion can be improved on a microscopic scale by the undulation of the substrate surface of the above Japanese Patent Application, there is room for further improvement of the bondage between the substrate and the gas-sensitive film on a microscopic scale. Also, the gas-sensitive film adhered in the manner of the above Japanese Patent Application is apt to produce uneven distribution of internal resistance along the boundary between the substrate and the gas-sensitive film. Moreover, impurities in the substrate and the electrodes tend to migrate to the boundary between the electrodes and the gas-sensitive film during operation, and the internal resistance of the boundary tends to increase accordingly. The uneven distribution of the internal resistance and increased internal resistance of the boundary result in deteriorating the performance characteristics of the gas sensor.

SUMMARY OF THE INVENTION

Therefore, an object of the invention is to obviate the above-mentioned shortcomings of the prior art by providing an improved thick-film gas sensor which has a stable internal resistance of the boundary between electrodes and a gas-sensitive film.

The inventors have noticed the fact that a planar or two-dimensional boundary between the electrode surface and the gas-sensitive film is susceptible to weakening of adhesion thereat due to stress acting thereon. The weakened adhesion tends to increase the internal resistance of the boundary.

The present invention stabilizes the internal resistance of the boundary between the electrodes and the gas-sensitive film by making the boundary threedimensional rather than two-dimensional.

To fulfil the above object, a thick-film gas sensor according to the present invention uses a pair of electrodes disposed on a same surface of a ceramic substrate with a spacing between the electrodes. A thick porous gassensitive film extends across those portions of the two electrodes which face to each other, so that the gassensitive film covers the surfaces of the above portions of the electrodes. Electrically conductive material, preferably platinum, is precipitated three-dimensionally around the electrodes on the boundaries between the electrodes and the gas-sensitive film, while retaining separation of the electrodes from each other so as to stabilize the electric connection of the electrodes to the gas-sensitive film.

In a preferred embodiment of the invention, the above-mentioned electrodes are embedded in the ceramic substrate, and an opening is bored at a surface portion of the substrate so as to expose the facing portions of the electrodes. The thick porous gassensitive film is formed in said opening of the substrate.

The invention provides a method of producing a thick-film gas sensor, in which method a pair of electrodes are disposed on a same surface of a ceramic substrate with a spacing between the electrodes, and a thick porous gas-sensitive film is formed on a same surface of the ceramic substrate across facing portions of the electrodes, which gas-sensitive film is processed by firing. The gas-sensitive film is impregnated with a solution of compound that mainly consists of platinum, and the thus impregnated gas-sensitive film is heated in a furnace so as to precipitate platinum three dimensionally around the electrodes on boundaries between the electrodes and the gas sensitive film while retaining separation of the electrodes from each other.

In a preferred embodiment of the method of the invention, the above-mentioned ceramic substrate has a first layer and a second layer, and the two electrodes are sandwiched between the first layer and the second layer of the substrate. The second layer of the ceramic substrate has an opening bored at such a position that the facing portions of the electrodes are exposed at the opening, and the gas-sensitive layer is formed in the above opening of the second layer of the substrate.

The ceramic substrate is a planar board made of ceramic material with a high heat resistivity, such as alumina, mullite, steatite, forsterite, and the like. The electrodes are disposed on the substrate, for instance by printing.

At least one pair of electrodes are used in the gas sensor of the invention, which electrodes are made of metallic material, preferably in the form of thick films. For use at an elevated temperature, metallic films mainly consisting of platinum (Pt) are preferred as the electrodes (to be referred to as Pt metallized electrodes hereinafter).

The thick porous gas-sensitive film (to be referred to as the gas-sensitive film hereinafter) consists essentially of oxides of transition metal whose electric resistance varies depending on the concentration of a gas to be detected in the surrounding atmosphere. Preferable oxides for a propane gas sensor and moisture sensor are tin oxide ($SnO_2$), zinc oxide ($ZnO$), ferric oxide ($Fe_2O_3$), while preferable oxides for an oxygen sensor are titanium oxide ($TiO_2$) and cobalt oxide ($CoO$).

As for the electrically conductive material to be precipitated on the boundary between the electrodes and the gas-sensitive film, any conductive substance which can be stuffed or precipitated on the boundary without causing any adverse effects on the gas-sensitive film can be used, provided that such substance adheres tightly to both the electrodes and the gas-sensitive film so as to ensure a high electric conductivity therebetween. Preferably, the electrically conductive material for this purpose is similar to that of the electrodes, and in the case of Pt metallized electrodes, platinum is the most preferable conductive material.

The boundary between the electrodes and the gas-sensitive film can be formed by disposing a porous gas-sensitive film on the substrate so as to come in contact with the electrode surface, firing the thus disposed film together with the substrate, impregnating the fired film with a solution containing the abovementioned electrically conductive material, and heating the impregnated film in a furnace so as to cause the conductive material to finely precipitate three dimensionally and continuously around and in the vicinity of the electrode surfaces.

An electrolytic process may be used before precipitating the conductive material three-dimensionally in the gas-sensitive film around the electrodes on the boundary between the electrodes and the gas-sensitive film; namely, the substrate carrying the electrodes and the gas-sensitive may be dipped in a solution containing the conductive material. Electroplating is effected while using the electrodes as cathodes, and then the conductive material is precipitated three-dimensionally in the gas-sensitive film around the electrodes on the boundary.

During operation of the thick-film gas sensor of the invention, the conductive material precipitated three-dimensionally in the gas-sensitive film around the electrodes on the boundary between the electrodes and the gassensitive film acts to form a three-dimensional connection therebetween so as to stabilize the contact resistance between them. Accordingly, unevenness and fluctuation of the internal resistance of such boundary are substantially eliminated.

BRIEF DESCRIPTION OF THE DRAWINGS

For a better understanding of the invention, reference is made to the accompanying drawings, in which:

FIG. 2, FIG. 3, FIG. 4, FIG. 5, FIG. 6, and FIG. 7 are schematic plan views, illustrating different steps of a method of producing a thick-film oxygen sensor according to the invention;

FIG. 2A, FIG. 3A, FIG. 4A, FIG. 5A, and FIG. 6A are end views which are taken along the arrows A-A of FIG. 2, FIG. 3, FIG. 4, FIG. 5, and FIG. 6 respectively;

FIG. 7A is a sectional view taken along the arrows A—A of FIG. 7;

Throughout different views of the drawings, 10 is a gas sensor, 11 is a gas-sensitive film, 12 is a body hardware element, 13 is a protector, 14 is an inner cylinder, 15 is a spacer, 16 is filler powder, 17 is a glass seal, 18 is a gasket, 19 is an outer cylinder, 20 is a seal, 21 through 23 are lead wires, 31 through 33 are terminals, 40 is a green sheet for a ceramic substrate first layer, 41 is a green sheet for a ceramic substrate second layer, 42 is a first ceramic layer green sheet, 43 is a second ceramic layer green sheet, 44 and 45 are electrode patterns, 46 is a resistive heater pattern, 47 through 49 are end portions, 51 through 53 are platinum lead wires, and 55 is an opening.

DESCRIPTION OF THE PREFERRED EMBODIMENT

The detailed structure of the gas sensor according to the invention will be described now by referring to an embodiment illustrated in the accompanying drawings, which embodiment is an oxygen sensor for detecting the oxygen concentration in exhaust gas from an internal combustion engine.

Figure 1:
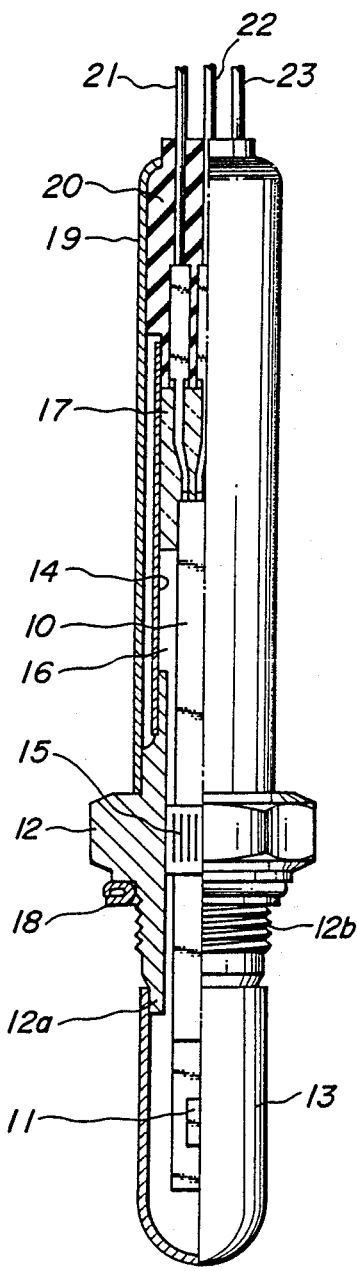
FIG. 1 is a partially cutaway side view of an oxygen detector which uses an oxygen sensor according to the present invention.

FIG. 1 shows a partially cutaway overall side view of an oxygen detector which uses a gas sensor of the invention. A gas sensor 10 of the invention, in the form of an oxygen sensor, has a thick porous gassensitive film 11 disposed on a ceramic substrate. The gas sensor 10 of this embodiment detects the oxygen concentration of gas being monitored. A cylindrical body hardware element 12, which is mountable on an internal combustion engine, houses the gas sensor 10 therein. A protector 13 is coupled to the engine-side end 12a of the body hardware element 12, so as to protect the gas sensor 10. The gas sensor 10 is held by an inner cylinder 14 which is carried by the body hardware element 12.

A spacer 15, filler powder 16, and a glass seal 17 are stuffed in the inner cylinder 14, so as to surround the gas sensor 10 for holding it in position.

To facilitate the mounting of the oxygen detector to an engine, the body hardware element 12 has a threaded portion 12b. Thus, the oxygen detector can be screwed to the engine with a gasket 18 disposed between the body hardware element 12 and the screwed portion of engine wall (not shown), so as to prevent engine exhaust gas from leaking through the screwed portion.

The filler powder 16, which is preferably a powder mixture consisting of talc and glass at a ratio of 1:1, acts to fix the gas sensor 10 in position within the inner cylinder 14. The glass seal 17 stuffed in the inner cylinder 14, which seal is preferably made of glass with a low melting point, acts to prevent the gas being monitored from leaking and to protect terminals of the gas sensor 10.

An outer cylinder 19 is coupled to the body hardware element 12 so as to cover the inner cylinder 14. A seal 20 made of silicone rubber is stuffed in the outer cylinder 19 at the upper end thereof, so as to protect and insulate both outgoing lead wires 21 through 23 and their joints with the terminals of the gas sensor 10 projecting from the glass seal 17. To facilitate the joining of the lead wires 21 through 23 with the terminals 31 through 33 (FIG. 8A) of the gas sensor 10, the seal 20 and the lead wires 21 through 23 may be placed in the inside of the outer cylinder 19 beforehand, and compressible connectors may be joined to the inner ends of the lead wires 21 through 23 respectively, and then the terminals 31 through 33 of the gas sensor 10 may be joined to the other ends of the compressible connectors.

Specimens of the gas sensor 10 were prepared by a process as shown in the plan views of FIG. 2 through FIG. 7. The end views of FIG. 2A through FIG. 6A are taken along the arrows A—A of the corresponding plan views of FIG. 2 through FIG. 6 respectively, while the sectional view of FIG. 7A is taken along the line A—A of FIG. 7. For clarity of the process of such preparation, the scale of the drawings of FIG. 2 through FIG.

Figure 8A:
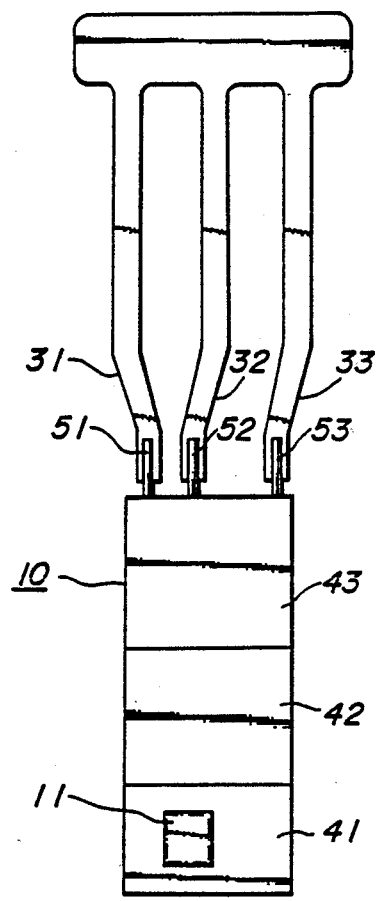
FIG. 8A is an explanatory diagram of connections between lead wires and terminals.
Figure 8B:
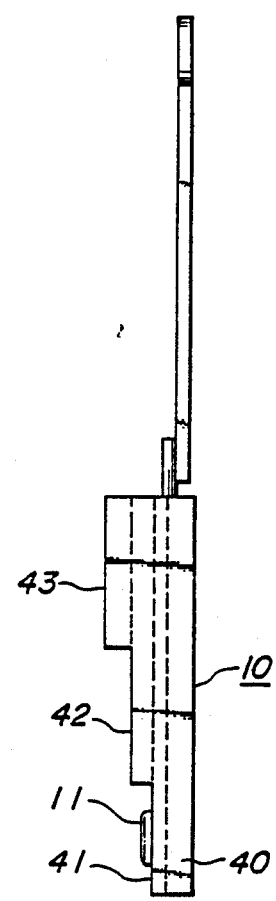
FIG. 8B is a side view of FIG. 8A.

7 is different from that of the above referred gas sensor 10 in FIG. 1 and from those of FIG. 8A and FIG. 8B.

A green sheet 40 for a ceramic substrate first layer, a green sheet 41 for a ceramic substrate second layer, a first ceramic layer green sheet 42, and a second ceramic layer green sheet 43 were formed in the following manner: 100 parts by weight of powder mixture was prepared by mixing 92% by weight (wt%) of alumina ($Al_2O_3$) with a mean particle diameter of 1.5 μm, 4 wt% of silica ($SiO_2$), 2 wt% of calcia ($CaO_2$), and 2 wt% of magnesia (MgO); 12 parts by weight of butyral resin and 6 parts by weight of dibutyl phthalate (DBP) were added to the 100 parts by weight of the powder mixture; a slurry was made by mixing the powder mixture after the above addition in an organic solvent; and the green sheets were formed from the slurry by using a doctor blade. The thickness of the green sheets was adjusted so as to produce the ceramic substrate first layer green sheet 40 with a 1 mm thickness, the ceramic substrate second layer green sheet 41 with a 0.2 mm thickness, a first ceramic layer green sheet 42 with a thickness of 0.8 mm, and the second ceramic layer green sheet 43 with a 0.8 mm thickness.

Electrically conductive patterns 44 through 49 were printed in the form of thick film patterns, on the same surface of green sheet 40 as FIGS. 2 and 3 show by using a platinum paste made by adding 7% of alumina ($Al_2O_3$) powder into platinum powder. Of such conductive patterns, electrode patterns 44 and 45 were for measuring the electric resistance of the above-mentioned gas-sensitive film 11, and a resistive heater pattern 46 was for heating the gas-sensitive film 11. End portions 47 through 49 were for applying an electric current to the resistive heater pattern 46 and extracting the output signal from the gas-sensitive film 11.

In preparing the gas sensor 10, electrode patterns 44, 45 and the resistive heater pattern 46 were at first printed on the green sheet 40 for a ceramic substrate first layer together with their end portions 47 through 49 by using the platinum paste, as shown in FIG. 2 and FIG. 2A. Thereafter, platinum lead wires 51 through 53 with a diameter of 0.2 mm were disposed on the end portions 47 through 49 of the patterns respectively, as shown in FIG. 3 and FIG. 3A.

As shown in FIG. 4 and FIG. 4A, an opening 55 was bored, for instance by punching, through the green sheet 41 for a ceramic substrate second layer at such a position that, when the green sheet 41 for the ceramic substrate second layer with the opening 55 thus bored was overlaid in position on the above-mentioned green sheet 40 so as to cover the entire pattern-printed surface of the latter sheet, the tip portions of the electrode patterns 44 and 45 were exposed to the outside through the opening 55. After being overlaid in the above manner, the green sheet 41 was joined to the green sheet 40 by heating and pressing. In the illustrated embodiment, the lamination formed of the thus joined two green sheets 40 and 41 corresponded to the abovementioned ceramic substrate. A gas-sensitive material was deposited in the opening 55 so as to provide the above-mentioned gas-sensitive film 11 of FIG. 1.

Referring to FIG. 5 and FIG. 5A, the first ceramic layer green sheet 42 was overlaid on the green sheet 41 of the above lamination and joined thereto by heating and pressing. A setback was provided in the first ceramic layer green sheet 42 as shown in FIG. 5. The second ceramic layer green sheet 43 was then over-laid on and joined to the first ceramic layer green sheet 42 by heating and pressing while forming a setback relative to the latter as shown in FIG. 6 and FIG. 6A. A staircaselike edge structure was thus formed at one end of the green sheets 40 and 41 for the ceramic substrate.

In the illustrated embodiment, the green sheets 42 and 43 thus joined to the green sheets 41 corresponded to a first ceramic layer f of FIG. 5A and a second ceramic layer s of FIG. 6A, respectively.

The surface portion of the green sheet 40 which faced the opening 55 of the green sheet 41 was roughened by scattering ceramic balls with a grain size of about 100 μm. The ceramic balls were made of the same material as the green sheets 40 and 41, so that undulation was provided on the above-mentioned surface portion of the green sheet 40.

Thus, a green lamination with the staircase-like edge structure was produced, in which the platinum lead wires 51 through 53 partially projected to the outside of the thus joined green sheets 40 and 41 while the tip portions of the electrodes patterns 44 and 45 were exposed to the outside through the opening 55 of the green sheet 41.

The above green lamination was fired at 1,500° C. in a furnace for two hours in air, so as to bake the green lamination into a ceramic substrate B carrying a first ceramic layer f and a second ceramic layer S integrally secured thereto, as shown in FIG. 7 and FIG. 7A.

Referring to FIG. 7 and FIG. 7A, a gas-sensitive film 11 was deposited on the fired ceramic substrate B through the opening 55. The finished thick-film gas sensor of laminar structure shown clearly in FIGS. 7, 7A, 8A and 8B was thus produced. To this end, a titania paste was prepared in the following manner; namely, 3 wt% of ethyl cellulose was added to 100 mole parts of titania ($TiO_2$) powder having a mean particle diameter of 1.2 μm and the mixture thus prepared was further mixed in BUTYL CARBITOL (a trademark of 2-(2-butoxy ethoxy ethanol) while controlling its viscosity so as to produce the titania paste with a viscosity of 300 poise. The titania paste was applied to the opening 55 by the thick film techniques so as to fill up the opening 55 while ensuring tight contact of the tip portions of the electrode patterns 44 and 45 with the titania paste. The ceramic lamination with the titania paste applied thereon was fired at 1,200° C. in a furnace for one hour in air, so that the titania paste was formed into the porous gas-sensitive film 11.

Three different specimens of the gas-sensitive film 11 were made in the following manner:

Specimen 1 (Reference):

Platinum (Pt) was added by dripping 2 μl of chloroplatinic acid (200 g/l) onto the gas-sensitive film 11 and heating it at 950° C. by a propane burner so as to cause rapid thermal decomposition. The gas-sensitive film 11 thus treated was of conventional type and carried platinum distributed uniformly throughout the porous structure thereof.

Specimen 2:

Platinum (Pt) was added by dripping 2 μl of chloroplatinic acid (200 g/l) onto the gas-sensitive film 11, heating it at 700° C. in a hydrogen furnace for 2 hours to cause thermal cracking, and dripping an additional 2 μl and then by applying the process of Specimen 1.

Specimen 3:

Platinum (Pt) was added at first by electroplating for 10 minutes through the use of chloroplatinic acid (200 g/l) and a voltage of 2 V applied across negative electrodes formed of the above-mentioned platinum lead wires 51, 52, 53 and a separately prepared platinum positive pole, and then by applying the process of Specimen 1.

The platinum lead wires 51 through 53 extending outwardly from the gas sensor 10 were connected to the terminals 31 through 33, respectively in a manner as shown in FIG. 8A. The terminals 31 through 33 with a runner joining them, made by etching a 0.3 mm thick nickel plate, were brought in contact with and welded to the platinum lead wires 51 through 53 respectively. The gas sensor 10 thus provided with the terminals 51 through 53 was placed in and secured to the inner cylinder 14 carried by the body hardware element 12 as shown in FIG. 1, so that a part of the substrate of the gas sensor 10 and the joint portions between the platinum lead wires 51 through 53 and the terminals 31 through 33 respectively were protected by the glass seal 17 fitted in the inner cylinder 14. Then, the three terminal 31 through 33 were severed from each other at suitable portions by removing the runner so as to provide the terminals of certain lengths. FIG. 8B is a side view of FIG. 8A as seen from the right.

In operation, heating power is applied to the resistive heater pattern 46 to heat up and activate the gas-sensitive film 11. The oxygen concentration can be determined by measuring the electric resistance of the gas-sensitive film 11 across the lead wires 22 and 23, which electric resistance depends on the oxygen concentration of the surrounding atmosphere.

The internal resistances of the three kinds of the gas-sensitive films 11, i.e., Specimens 1, 2, and 3, were measured. Initial values of them were measured while keeping the gas-sensitive films 11 in a propane burner with a theoretical air fuel ratio $\lambda = 0.9$ and with a gas temperature of 350° C.

The values of the internal resistances after ON-OFF durability test were measured after applying heat cycle test of 5-minute heating in a Bunsen burner with a gas temperature of 900° C. followed by 5-minute cooling.

During the measurements and the durability test, +12 V was applied to the platinum lead wire 51 while the platinum lead wire 53 was grounded, and a fixed resistance to 50 k$\Omega$ was connected across the platinum lead wires 52 and 53. After the above-mentioned measurements, recovery characteristics were tested by reversing the connections to the positive and negative electrodes and leaving the gas-sensitive films 11 in open air for 5 hours. The values of the internal resistances after the recovery tests were also measured.

The result is shown in Table 1. t,180

As can be seen from Table 1, in the case of the gas-sensitive film of the invention, the internal resistance after ON-OFF durability test is stabilized. In the case of the Reference Specimen 1, the internal resistance is remarkably recovered after the recovery test, and the reason for the large internal resistance after the durability test appears to be in that impurities in the substrate and the gas-sensitive film are concentrated on the boundary surfaces between the electrodes and the gas-sensitive film upon application of the d.c. voltage across the electrodes and the internal resistance of the boundary increases. Accordingly, the invention which improves the electric conductivity at the above boundary can provide a considerable improvement in the stability of the internal resistance of the above boundary over the conventional structures, as proved by the comparison of the measured data of Specimens 2 and 3 against those of Specimen 1.

It is inferred that, in Specimens 2 and 3 of the invention, platinum as a conductive material is precipitated three-dimensionally in the gas-sensitive film around the electrodes on the boundary between Pt electrodes and titania gas-sensitive film, and the boundaries between the Pt electrodes and the titania gas-sensitive film and around the electrodes are stuffed with the thus precipitated platinum, so as to provide a three-dimensional electric connection thereat.

As described in the foregoing, a thick-film gas sensor according to the invention provides a remarkable improvement in the performance stability and durability, and the method according to the invention facilitates stable and efficient production of the thick-film gas sensor with excellent performance characteristics.

What is claimed is:

1. A thick-film gas sensor of laminar structure comprising:
    a ceramic substrate,
    a pair of electrodes disposed on a same surface of the ceramic substrate with a spacing therebetween,
    a thick porous gas-sensitive film consisting essentially of a gas-sensitive metal oxide extending across facing portions of the electrodes, and
    an electrically conductive material precipitated three dimensionally in the thick porous gas-sensitive film around the electrodes on boundaries between the electrodes and the gassensitive film so that reliable electric connections of the electrodes to the gas-sensitive film and a stable gas-sensitive film internal resistance are provided.

2. A thick-film gas sensor of laminar structure comprising:
    a ceramic substrate,
    a pair of electrodes disposed on a same surface of the ceramic substrate with a spacing therebetween,
    a thick porous gas-sensitive film consisting essentially of a gas-sensitive metal oxide extending across facing portions of the electrodes, and
    an electrically conductive material precipitated three dimensionally in the thick porous gas-sensitive film around the electrodes on boundaries between the electrodes and the gassensitive film so as to provide reliable electric connections of the electrodes to the gas-sensitive film, said electrodes being embedded in the ceramic substrate, the ceramic substrate having an opening bored at a surface portion thereof so as to expose facing portions of the electrodes, and said thick porous gas-sensitive film being formed in said opening of the substrate.

3. A thick-film gas sensor as defined by claim 1 wherein said electrodes and said electrically conductive material are platinum.

4. A thick film gas sensor as defined by claim 3 wherein spaces between each of said electrodes and said gas-sensitive film are filled with the precipitated electrically conductive material.

5. A thick-film gas sensor as defined by claim 1, wherein the internal resistance of the gas-sensitive film measured after the film is subjected to a gas temperature of 900° C. for five minutes and then cooled is no more than approximately 1.1 kiloohms greater than an initial internal resistance of the gas-sensitive film measured while the film is subjected to a gas temperature of 350° C.

6. A thick-film gas sensor as defined by claim 5, wherein the internal resistance of the gas-sensitive film measured after a positive connection to one of said electrodes is reversed with a negative connection to the other of said electrodes and after the film is left in open air for five hours is no more than approximately 1.6 kiloohms greater than said initial internal resistance.

7. A thick-film gas sensor of laminar structure comprising:
- a ceramic substrate,
- a pair of electrodes disposed on a same surface of the ceramic substrate with a spacing therebetween,
- a thick porous gas-sensitive film consisting essentially of a gas-sensitive metal oxide extending across facing portions of the electrodes, and
- an electrically conductive material finely precipitated three dimensionally and continuously in the thick porous gassensitive film around the electrodes on boundaries between the electrodes and the gas-sensitive film so that reliable electric connections of the electrodes to the gas-sensitive film and a stable gas-sensitive film internal resistance are provided.

* * * * *